United States Patent
Arndt et al.

(10) Patent No.: US 7,630,074 B2
(45) Date of Patent: Dec. 8, 2009

(54) DEVICE AND METHOD FOR MEASURING AT LEAST ONE PARAMETER OF PARTICLES IN A FLUID

(75) Inventors: Michael Arndt, Allendorf (DE); Maximilian Sauer, Constance (DE); Alexander Graf, Immenstaad (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 12/148,718

(22) Filed: Apr. 21, 2008

(65) Prior Publication Data

US 2008/0266566 A1      Oct. 30, 2008

Related U.S. Application Data

(63) Continuation of application No. 11/900,719, filed on Sep. 12, 2007, now abandoned.

(30) Foreign Application Priority Data

Sep. 13, 2006   (DE)  ...................... 10 2006 043 013

(51) Int. Cl.
  *G01N 15/02*   (2006.01)
(52) U.S. Cl. ..................................... 356/335
(58) Field of Classification Search .......... 356/335–343
  See application file for complete search history.

(56) References Cited

U.S. PATENT DOCUMENTS

| | | | | |
|---|---|---|---|---|
| 4,441,816 A | * | 4/1984 | Hencken et al. | 356/335 |
| 4,664,513 A | * | 5/1987 | Webb et al. | 356/28 |
| 4,679,939 A | * | 7/1987 | Curry et al. | 356/336 |
| 2004/0201845 A1 | * | 10/2004 | Quist et al. | 356/338 |

FOREIGN PATENT DOCUMENTS

EP      0 783 101 A2      7/1997

* cited by examiner

*Primary Examiner*—Michael P Stafira
(74) *Attorney, Agent, or Firm*—Kenyon & Kenyon LLP

(57) ABSTRACT

A device and a method for measuring at least one parameter of particles in a fluid, the device having a radiation source and a radiation sensor, the device having a fluid region that is in contact with the fluid; the radiation source being provided for the emission of measuring radiation according to a first direction onto the fluid region, the radiation sensor being provided for the detection of a measuring radiation reflected away from the fluid region in a second direction; furthermore, the radiation sensor having a plurality of sensor elements; and the spectral sensitivity of different sensor elements being developed differently for a wavelength-sensitive detection of the reflected measuring radiation.

25 Claims, 3 Drawing Sheets

DEVICE AND METHOD FOR MEASURING AT LEAST ONE PARAMETER OF PARTICLES IN A FLUID

CROSS-REFERENCE TO RELATED APPLICATION

This application is a Continuation Application of prior U.S. patent application Ser. No. 11/900,719 filed Sep. 12, 2007 now abandoned, which claims priority to German Patent Application No. 10 2006 013.1 filed on Sep. 13, 2006, all of which are incorporated herein by reference in their entirety.

RELATED APPLICATION INFORMATION

The present application is based on and claims the benefit of and priority to German patent application no. 10 2006 043 013.1, which was filed in Germany on Sep. 13, 2006, and the disclosure of the foregoing German patent application is incorporated herein by reference.

FIELD OF THE INVENTION

The present invention relates to a device for measuring at least one parameter of particles in a fluid.

BACKGROUND INFORMATION

A method and a device are discussed in European Patent Application EP 0 783 101 A2 for the optical concentration measurement of fine dust in a medium. In this instance, polarized light is specifically supplied to the medium containing the particles, and then the scattered light intensities of the scattered light that is coupled out are measured. This known device for the optical measurement of the concentration of fine dust has the disadvantage that several polarization filters and collimation lenses are required, and therefore the manufacture of such a device is connected with a comparatively great expenditure.

SUMMARY OF THE INVENTION

By contrast, the device according to the exemplary embodiments and/or exemplary methods of the present invention, having the features described herein, has the advantage that a simple method is available for determining the properties of a fluid encumbered with particles by using different wavelength-selective filters. In this case, the parameters of the particles that come into consideration are particularly the latter's size, their shape, their type or their density within the fluid. A gas is especially designated as the fluid, so that applications such as the characterization of particle-encumbered exhaust gases or the like are possible, according to the exemplary embodiments and/or exemplary methods of the present invention. In addition, however, liquids might be considered, for instance, engine oil or other liquids, particularly within a motor vehicle.

According to the exemplary embodiments and/or exemplary methods of the present invention, the device may have a micromechanical radiation sensor or that the radiation sensor have micromechanical sensor elements. According to the exemplary embodiments and/or exemplary methods of the present invention, it is thereby possible to achieve a functional integration in a small space, so that the device according to the present invention is able to be produced in a manner that is particularly compact as to installation space, is weight-saving and is cost-effective.

According to the exemplary embodiments and/or exemplary methods of the present invention, the device may also have an absorption element, and the absorption element may be provided bordering on the fluid region. This may advantageously avoid that, except for the measuring radiation reflected by the particles, no portion of light or portion of radiation reaches the location of the radiation sensor. In particular, it is thereby advantageously ruled out to the greatest extent possible, according to the present invention, that light starting directly from the radiation source or equivalent radiation reaches the region of the detector.

If the measuring radiation is provided, it may be in the visible wavelength range and/or in the near infrared range and/or in the far infrared range. This makes it possible, according to the exemplary embodiments and/or exemplary methods of the present invention, to obtain a plurality of data about the fluid and the particles located in it, by a variation of the various spectral detection windows used, so that corresponding particle parameters are obtainable in large numbers and having comparatively high accuracies.

According to the exemplary embodiments and/or exemplary methods of the present invention, each of the sensor elements in each case may have at least one radiation filter for setting the spectral sensitivity. Because of this feature, it is particularly simply and economically possible to specify the spectral detection windows and to vary them.

Furthermore, according to the exemplary embodiments and/or exemplary methods of the present invention, the sensor elements may have a layer absorbing radiation and/or a thermopile element. For this, one may fall back upon tested technologies for producing radiation detectors, so that the device according to the present invention may be produced in an especially economical manner.

A further subject matter of the exemplary embodiments and/or exemplary methods of the present invention is a method for measuring at least one parameter of particles in a fluid using a device according to the present invention. It is thereby advantageously possible, according to the exemplary embodiments and/or exemplary methods of the present invention, to carry out a combined evaluation of the signals of the different sensor elements that are sensitive to different spectral wavelength ranges, and thus to attain a plurality of data concerning the particles contained in the fluid.

Exemplary embodiments of the present invention are shown in the drawings and are explained in greater detail in the following description.

DETAILED DESCRIPTION

Figure 1:
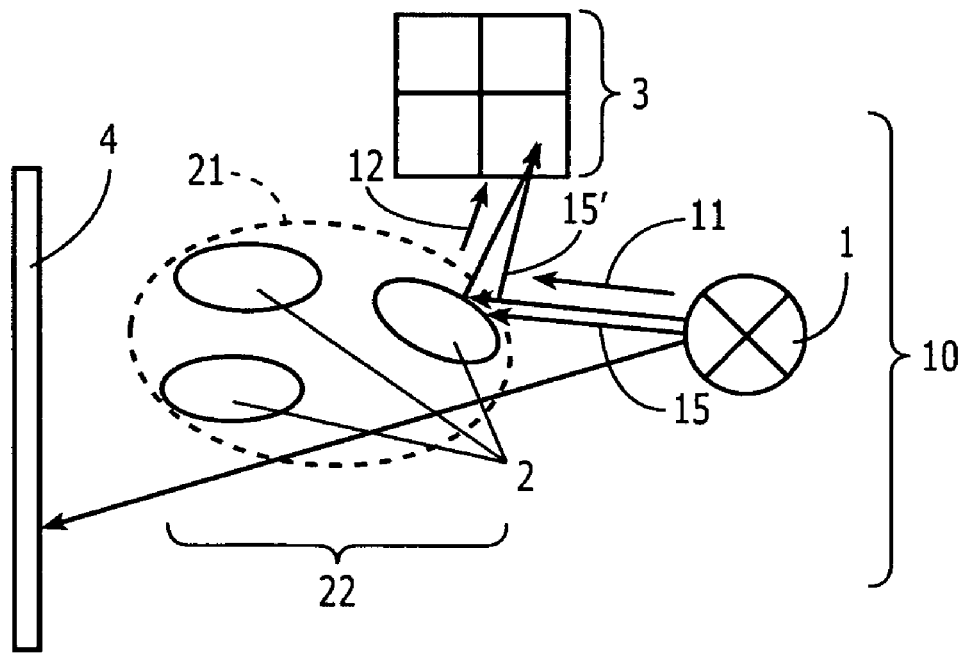
FIG. 1 shows a schematic representation of the various elements of the device according to the present invention, according to a first specific embodiment.

FIG. 1 shows a schematic representation of a first specific embodiment of a device 10 according to the present invention. Device 10 has a radiation source 1 which radiates measuring radiation 15 in a first direction 11 onto a fluid region 22. In fluid region 22 there is a fluid 21 which is encumbered with particles, that is, fluid 21 has particles 2 in it. Particles 2 reflect measuring rays 15 and thereby generate a reflected measuring radiation 15', which is radiated in a second direction 12 that is changed compared to first direction 11, first direction 11, for example, forming an angle with second direction 12 in a range of about 20° to about 160°, which may be between about 40° and about 140°, and particularly may be between 60° and 120°. The reflected measuring radiation 15', that is radiated or rather reflected in the direction of a radiation sensor 3 by particles 2, is used to measure the properties or parameters of particles 2. An absorption element 4 or an absorber 4 is used to absorb measuring radiation 15. This makes it advantageously possible for no measuring radiation 15 to reach the region of radiation sensor 3 directly or indirectly (except for by reflection at the particles).

Figure 2:
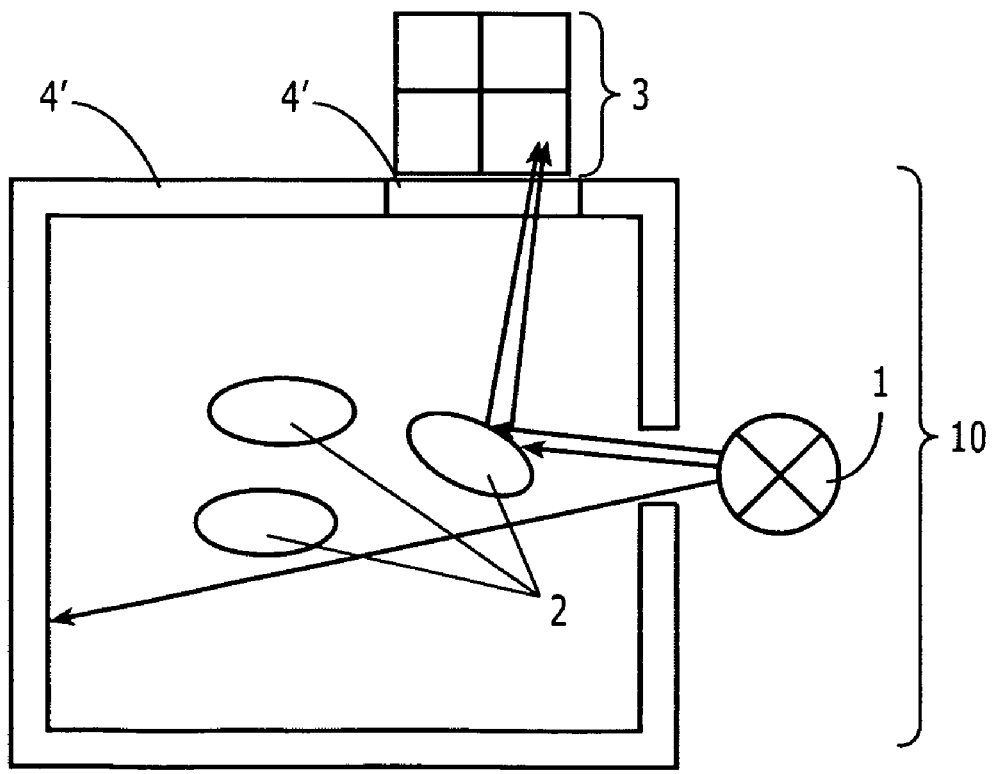
FIG. 2 shows a schematic representation of the device according to the present invention of a second specific embodiment.

FIG. 2 shows a second specific embodiment of device 10 according to the exemplary embodiments and/or exemplary methods of the present invention. This again has radiation source 1, particles 2, radiation sensor 3 and absorber 4 or absorption element 4. Absorber 4 is provided essentially around the region of fluid 21, in this instance. This considerably reduces the probability that light of the measuring radiation, that is not reflected by the particles, falls on the radiation sensor. Between the enclosure of fluid 21 and radiation sensor 3, a radiation-transmitting window 4' may be provided, or even an opening 4' may be provided.

Figure 3:
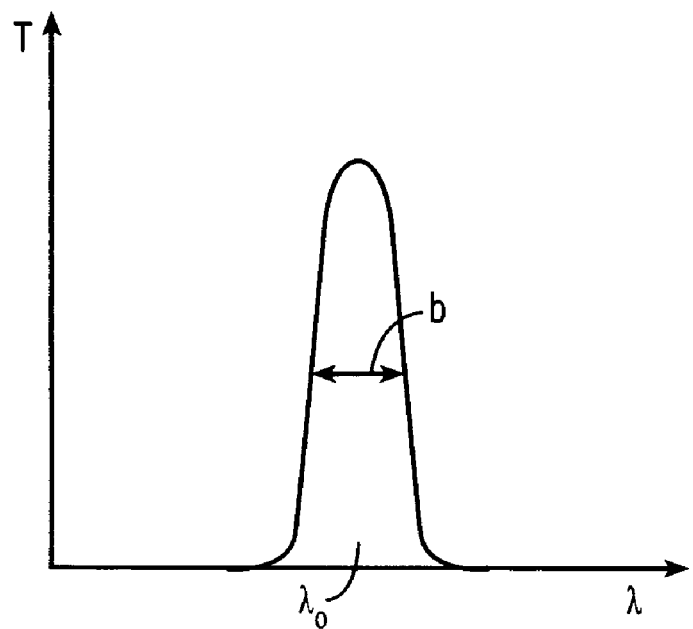
FIG. 3 shows a schematic representation of the transmission curve of a filter element of the wavelength-selective sensitivity of a sensor element.

FIG. 3 shows a typical example of the transmission characteristics of a filter used for producing the wavelength-selective detection of different sensor elements of the radiation sensor. The transmission in percent is plotted in the ordinate direction. Wavelength λ is plotted in the direction of the abscissa. The filter transmits radiation in the wavelength range about a specified wavelength $\lambda_0$. The width of the transmitting range is designated by reference symbol b.

Figure 4:
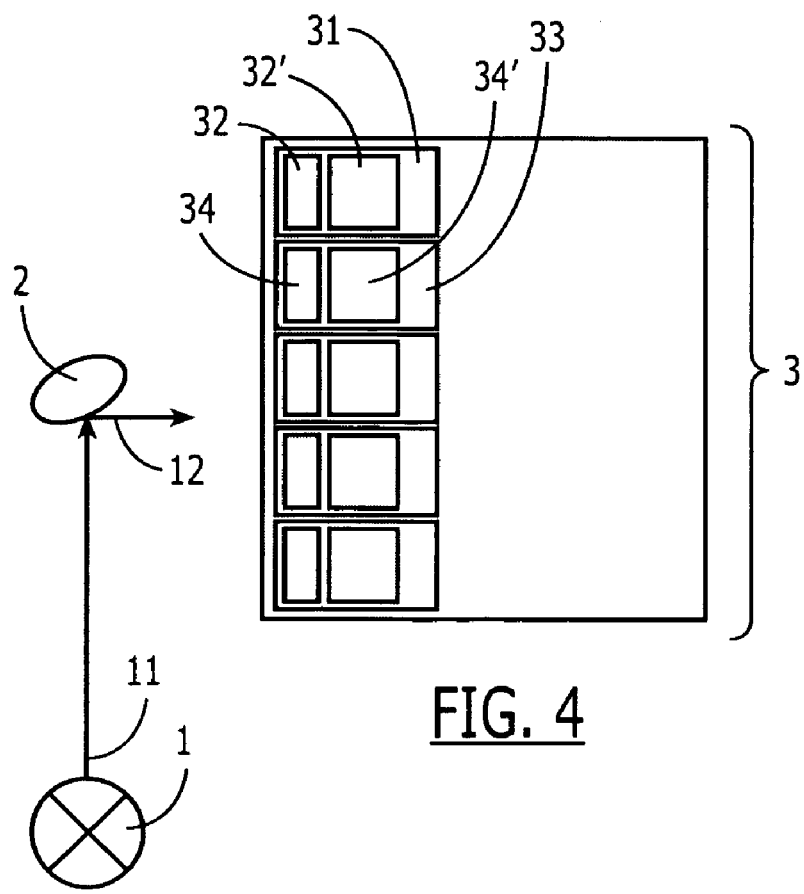
FIG. 4 shows a schematic representation of the construction of the radiation sensor.

FIG. 4 shows a schematic representation of radiation sensor 3, which includes a plurality of sensor elements, only two sensor elements 31 and 33 being designated by a reference symbol, for simplicity's sake. To produce a wavelength-selective detection of reflected radiation 15', sensor elements 31, 33 may each have a filter element 32, 34, or rather a radiation filter 32, 34, according to the exemplary embodiments and/or exemplary methods of the present invention. The actual sensing structure, which detects the radiation transmitted by filter 32, 34, is shown schematically in FIG. 4 by reference symbols 32' and 34'. The sensing structure is situated along second direction 12 (along the direction of reflected measuring radiation 15'), behind radiation filter 32, 34. For instance, radiation filters 32, 34 have essentially transmission characteristics shown in FIG. 3, for different radiation filters 32, 34, however, at least one of the parameters for describing the transmission characteristics, namely, central wavelength $\lambda_0$, and the width of spectral transmitting window b being changed.

The exemplary embodiments and/or exemplary methods of the present invention makes it possible to obtain a plurality of data concerning particles 2 and fluid 21, by the evaluation of different wavelength ranges of reflected measuring radiation 15', which, according to the present invention, can also take place in a more or less continuous process, and does not, for example, require carrying out discontinuous measuring methods.

In particular it may be provided, according to the exemplary embodiments and/or exemplary methods of the present invention, that the transmission characteristics of a plurality of filters are spectrally situated in such a way that a spectral overlap of the transmission characteristics of the individual filters comes about, for instance, because in response to an approximately equal width b of the spectral transmission window, the central wavelengths of different (individual) filters are provided to be at a distance of half the width b. In this case, according to the present invention, it is possible, for example, to evaluate very well the presence of particles with the aid of modern pattern recognition algorithms, because the particles in the fluid demonstrate a specific reflection pattern.

Figure 5:
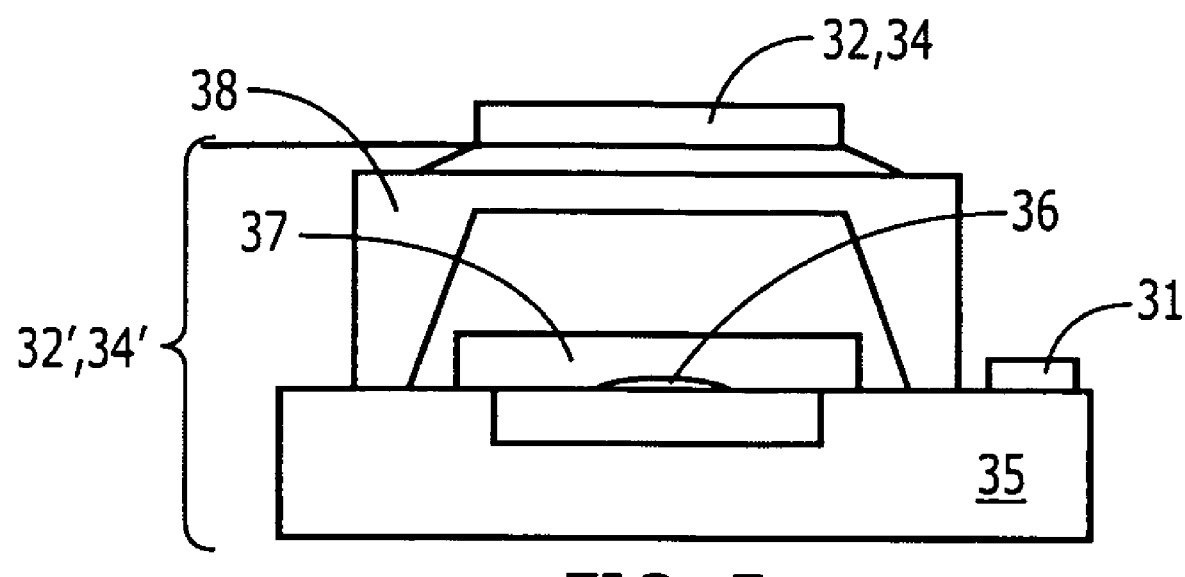
FIG. 5 shows an example of a sensor element in a side view.

Sensor elements 31, 33 may be produced by micropatterning technique or micromechanically. FIG. 5 shows a side view of such a sensor element 31, 33 that is produced using the technique of surface micromechanics. It includes a substrate material 35 and has a diaphragm and a temperature-sensitive thermopile element 36. However, on the diaphragm there may also be present a pyroelectric layer. Thermopile element 36, whose lower side is fastened to the diaphragm, is covered laterally and above by a radiation-absorbing layer 37. The thermopile structure is, for instance, sealed gas-tight by a cap 38, so that a cavity forms between the diaphragm and the substrate material on the one hand, and also between cap 38 and radiation-absorbing layer 37 on the other hand. In these regions a vacuum may be provided. Filter 32, 34 is mounted on cap 38, according to the example shown, for instance, adhesively, this filter 32, 34 only transmitting a specified wavelength range, according to the transmission characteristics of the filter. The sensor element is connected via terminals 39 (so-called bondlands) to an evaluation circuit that is not shown. According to the exemplary embodiments and/or exemplary methods of the present invention, it is advantageous in this instance that the use of another filter type is comparatively easily possible, and that this can be done simply by adhering on another filter flake. This clearly reduces the production costs of a device according to the present invention.

In principle, however, all types of sensor elements 31, 33, perhaps components produced by so-called bulk micromechanics, may be used. Sensor elements 31, 33 are located either in individual housings or in an overall housing, according to the present invention. According to the present invention, radiation sensor 3 may include a plurality of such sensor elements, which differ essentially exclusively with respect to the filters or rather radiation filters 32, 34. The type of radiation filter 32, 34 that is to be used may be determined as follows: If the substance that is to be tested or classified using radiation sensor 3 is known, then this substance is tested using an analytical technique, such as FTIR spectroscopy (Fourier transform infrared spectroscopy). An attempt is now made in these tests to find certain wavelengths which permit obtaining evidence about content substances or parameters of the content substances, or rather, the particles, perhaps the shape of the particles and the size distribution of the particles or the like.

Some applications of the device according to the present invention are, for example, determining the condition of operating liquids of an automobile, such as engine oil, fuel, cooling liquids, brake fluid or the like, classifying operating liquids such as fuel, gasoline, Diesel, RME (rape seed methyl ester) or determining the condition or the classification of gases or of particle-encumbered gases inside or outside an automobile, such as the internal air, the external air, the exhaust gas, or the like. Furthermore, using the exemplary embodiments and/or exemplary methods of the present invention, a determination of the condition and a classification or generally a measurement of at least one parameter of a particle in a fluid may be used for such fluids that might be used in the medical field, such as breathed air or the like.

What is claimed is:

1. A device for measuring at least one parameter of particles in a fluid, comprising:
   a radiation source;
   a radiation sensor; and
   a fluid region that is in contact with the fluid;
   wherein the radiation source is provided for an emission of measuring radiation according to a first direction onto the fluid region,
   wherein the radiation sensor is provided for detecting a measuring radiation reflected away from the fluid region in a second direction, and
   wherein the radiation sensor has a plurality of sensor elements, the plurality of sensor elements ascertaining the at least one parameter of the particles, and the spectral sensitivity of different sensor elements being developed differently for a wavelength-sensitive detection of the reflected measuring radiation.

2. The device of claim 1, wherein the device has a micromechanical radiation sensor or the radiation sensor has micromechanical sensor elements.

3. The device of claim 1, wherein the device has an absorption element.

4. The device of claim 1, wherein the measuring radiation is at least in one of a visible wavelength range, a near infrared range, and a far infrared range.

5. The device of claim 1, wherein each of the sensor elements has in each case at least one radiation filter for setting the spectral sensitivity.

6. The device of claim 1, wherein the radiation filters only transmit a specified wavelength.

7. The device of claim 1, wherein the sensor elements have at least one of a radiation-absorbing layer and a thermopile element.

8. A method for measuring at least one parameter of particles in a fluid, the method comprising:
   using a device for measuring at least one parameter of particles in a fluid, the device including:
      a radiation source;
      a radiation sensor; and
      a fluid region that is in contact with the fluid;
      wherein the radiation source is provided for an emission of measuring radiation according to a first direction onto the fluid region,
      wherein the radiation sensor is provided for detecting a measuring radiation reflected away from the fluid region in a second direction, and
      wherein the radiation sensor has a plurality of sensor elements, the spectral sensitivity of different sensor elements being developed differently for a wavelength-sensitive detection of the reflected measuring radiation; and
   ascertaining the at least one parameter of the particles with measuring signals of the plurality of sensor elements of the radiation sensor, the at least one parameter including at least one of a particle size, a particle shape, a particle type and a particle density, and being measured within the fluid.

9. The device of claim 1, wherein the device has an absorption element, which borders on the fluid region.

10. The device of claim 1, wherein a plurality of spectral detection windows obtain data about the fluid.

11. The device of claim 1, wherein the plurality of sensor elements are produced by a micropatterning technique.

12. The device of claim 1, wherein the device has an absorption element, which borders on the fluid region, wherein a plurality of spectral detection windows obtain data about the fluid, and wherein the plurality of sensor elements are produced by a micropatterning technique.

13. The device of claim 1, wherein the device has a micromechanical radiation sensor or the radiation sensor has micromechanical sensor elements, wherein the device has an absorption element, wherein the measuring radiation is at least in one of a visible wavelength range, a near infrared range, and a far infrared range, wherein each of the sensor elements has in each case at least one radiation filter for setting the spectral sensitivity, wherein the radiation filters only transmit a specified wavelength, and wherein the sensor elements have at least one of a radiation-absorbing layer and a thermopile element.

14. The device of claim 13, wherein the device has an absorption element, which borders on the fluid region, wherein a plurality of spectral detection windows obtain data about the fluid, and wherein the plurality of sensor elements are produced by a micropatterning technique.

15. The method of claim 8, wherein the device has a micromechanical radiation sensor or the radiation sensor has micromechanical sensor elements.

16. The method of claim 8, wherein the device has an absorption element.

17. The method of claim 8, wherein the measuring radiation is at least in one of a visible wavelength range, a near infrared range, and a far infrared range.

18. The method of claim 8, wherein each of the sensor elements has in each case at least one radiation filter for setting the spectral sensitivity.

19. The method of claim 8, wherein the radiation filters only transmit a specified wavelength.

20. The method of claim 8, wherein the sensor elements have at least one of a radiation-absorbing layer and a thermopile element.

21. The method of claim 8, wherein the device has an absorption element, which borders on the fluid region.

22. The method of claim 8, wherein a plurality of spectral detection windows obtain data about the fluid.

23. The method of claim 8, wherein the plurality of sensor elements are produced by a micropatterning technique.

24. The method of claim 8, wherein the device has a micromechanical radiation sensor or the radiation sensor has micromechanical sensor elements.

25. The method of claim 8, wherein the device has an absorption element, wherein the measuring radiation is at least in one of a visible wavelength range, a near infrared range, and a far infrared range, wherein each of the sensor elements has in each case at least one radiation filter for setting the spectral sensitivity, wherein the radiation filters only transmit a specified wavelength, wherein the sensor elements have at least one of a radiation-absorbing layer and a thermopile element, wherein the device has an absorption element, which borders on the fluid region, wherein a plurality of spectral detection windows obtain data about the fluid, and wherein the plurality of sensor elements are produced by a micropatterning technique.

* * * * *